United States Patent
Mass et al.

(10) Patent No.: US 7,096,068 B2
(45) Date of Patent: Aug. 22, 2006

(54) USER-ATTACHABLE OR DETACHABLE TELEMETRY MODULE FOR MEDICAL DEVICES

(75) Inventors: William R. Mass, Maple Grove, MN (US); Mark D. Amundson, Cambridge, MN (US); Jeffrey A. Von Arx, Minneapolis, MN (US); Prashant Rawat, Saint Paul, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 478 days.

(21) Appl. No.: 10/052,496

(22) Filed: Jan. 17, 2002

(65) Prior Publication Data

US 2003/0135246 A1 Jul. 17, 2003

(51) Int. Cl.
*A61N 1/362* (2006.01)
(52) U.S. Cl. .......................... 607/32; 607/60
(58) Field of Classification Search ............. 607/36, 607/37, 38, 30–33, 59, 60
See application file for complete search history.

(56) References Cited

U.S. PATENT DOCUMENTS

| | | | |
|---|---|---|---|
| 4,407,288 A | | 10/1983 | Langer et al. |
| 5,314,452 A | * | 5/1994 | Hirschberg et al. ............ 607/36 |
| 5,342,408 A | * | 8/1994 | deCoriolis et al. ............. 607/32 |
| 5,383,914 A | * | 1/1995 | O'Phelan ...................... 607/38 |
| 5,411,538 A | * | 5/1995 | Lin ............................. 607/36 |
| 5,476,488 A | * | 12/1995 | Morgan et al. ................ 607/32 |
| 5,545,188 A | * | 8/1996 | Bradshaw et al. ............. 607/37 |
| 5,556,421 A | * | 9/1996 | Prutchi et al. ................ 607/36 |
| 5,679,026 A | * | 10/1997 | Fain et al. .................... 439/651 |
| 5,861,019 A | * | 1/1999 | Sun et al. ...................... 607/60 |
| 5,904,708 A | * | 5/1999 | Goedeke ....................... 607/18 |
| 6,006,135 A | * | 12/1999 | Kast et al. ..................... 607/37 |
| 6,167,312 A | * | 12/2000 | Goedeke ....................... 607/60 |
| 6,236,889 B1 | * | 5/2001 | Soykan et al. ................. 607/30 |
| 6,240,317 B1 | * | 5/2001 | Villaseca et al. .............. 607/60 |
| 6,567,703 B1 | * | 5/2003 | Thompson et al. ............ 607/36 |
| 6,675,049 B1 | * | 1/2004 | Thompson et al. ............ 607/60 |
| 6,721,602 B1 | * | 4/2004 | Engmark et al. .............. 607/36 |
| 6,792,312 B1 | * | 9/2004 | Bruchmann et al. ........... 607/37 |
| 6,920,360 B1 | * | 7/2005 | Lee et al. ...................... 607/60 |

OTHER PUBLICATIONS

Capps, Charles, "Near field or far field?", EDN, www.ednmag.com, (Aug. 16, 2001), 5 pgs.

\* cited by examiner

*Primary Examiner*—Jeffrey R. Jastrzab
(74) *Attorney, Agent, or Firm*—Schwegman, Lundberg, Woessner & Kluth, P.A.

(57) ABSTRACT

An implantable, self-contained, user-attachable or detachable telemetry module plugs into an implantable medical device to provide or supplement one or more telemetry functions needed by a patient having certain health conditions. A user-attachable or detachable telemetry module allows a user, such as a physician or other care provider, to select a telemetry module and attach it to a medical device. Various types of telemetry are implemented as various user-attachable or detachable telemetry modules, each providing one or more telemetry functions suitable for a particular patient whose condition imposes a particular demand on telemetry. A care provider selects a user-attachable or detachable telemetry module most suited for the particular patient, which improves healthcare cost efficiency. One example of user-attachable or detachable telemetry module includes a radio-frequency (RF) transmitter-receiver circuit module and a lead carrying an antenna. In one example, the circuit module is away from the implantable medical device and coupled to the implantable medical device through the lead. In another example, the circuit module directly attaches to the implantable medical device.

47 Claims, 13 Drawing Sheets

USER-ATTACHABLE OR DETACHABLE TELEMETRY MODULE FOR MEDICAL DEVICES

TECHNICAL FIELD

The present system relates generally to implantable medical devices and particularly, but not by way of limitation, to such a device including a telemetry system allowing communication with an external device.

BACKGROUND

Medical devices are implanted in human bodies to perform tasks including, for example, monitoring physiological conditions, diagnosing diseases, treating diseases, or restoring functions of organs or tissues. Examples of such implantable medical devices include cardiac rhythm management systems, neurological stimulators, neuromuscular stimulators, and drug delivery systems. Because such a device may be implanted in a patient and typically remain therein for a long time, even up to the patient's life expectancy, the size and power consumption of the device are inherently constrained. Consequently, an implantable device may depend on an external system to perform certain functions. A function of a device providing communication between the implantable device and the external system is referred to as telemetry. Examples of specific telemetry functions include programming the implantable device to perform certain monitoring or therapeutic tasks, extracting an operational status of the implantable device, transmitting real-time physiological data acquired by the implantable device, and extracting physiological data acquired by and stored in the implantable device.

In certain instances, the patient's health condition may determine the amount of telemetry activity between the implantable device and the external system. For example, an implantable device stabilizing a body function of an already stable patient may need infrequent telemetry during follow-ups. However, an implantable device worn by a very ill patient to treat an unstable, life-threatening condition may need frequent telemetry for monitoring and/or device-reprogramming. The amount of telemetry activity also depends on the type of the implantable device. A self-contained device performing relatively simple tasks may require only infrequent check-ups. A device performing complicated tasks, such as frequent real-time data processing, may require access to an external system having computing capabilities required for the task. Such a device may require frequent or even continuous telemetry.

One particular example of implantable medical devices is a cardiac rhythm management device implanted in a patient to treat irregular or other abnormal cardiac rhythms by delivering electrical pulses to the patient's heart. Such rhythms result in diminished blood circulation. Implantable cardiac rhythm management devices include, among other things, pacemakers, also referred to as pacers. Pacers are often used to treat patients with bradyarrhythmias, that is, hearts that beat too slowly or irregularly. Such pacers may coordinate atrial and ventricular contractions to improve the heart's pumping efficiency. Implantable cardiac rhythm management devices also include devices providing cardiac resynchronization therapy (CRT), such as for patients with congestive heart failure (CHF). CHF patients have deteriorated heart muscles that display less contractility and cause unsynchronized heart contraction patterns. By pacing multiple heart chambers or sites, CRT device restores a more synchronized contraction of the weakened heart muscle, thus increasing the heart's efficiency as a pump. Implantable cardiac management devices also include defibrillators that are capable of delivering higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias, that is, hearts that beat too quickly. In addition to pacers, CRT devices, and defibrillators, implantable cardiac rhythm management systems also include, among other things, pacer/defibrillators that combine the functions of pacers and defibrillators, drug delivery devices, and any other implantable systems or devices for diagnosing or treating cardiac arrhythmias.

Typically, an implantable cardiac rhythm management device communicates, via telemetry, with an external device referred to as a programmer. One type of telemetry is based on inductive coupling between two closely-placed coils using the mutual inductance between these coils. This type of telemetry is referred to as inductive telemetry or near-field telemetry because the coils must typically be closely situated for obtaining inductively coupled communication.

In one example, an implantable device includes a first coil and a telemetry circuit, both sealed in a metal housing (referred to as a "can"). An external programmer provides a second coil in a wand that is coupled to the programmer. During device implantation, a physician evaluates the patient's condition, sometimes by using the implanted device to acquire real-time physiological data from the patient and communicating the physiological data in real-time to the external programmer for processing and/or display. The physician may also program the implantable device, including selecting a pacing or defibrillation therapy mode and parameters required by that mode based on the patient's condition and needs. The data acquisition and device programming are both performed via the inductive telemetry. If the patient's condition is stable after implantation, he or she needs no attention from the physician or other care provider until a scheduled routine follow-up. During a typical routine follow-up, the physician reviews the patient's history with the implantable device, re-evaluate the patient's condition, and re-program the implantable device if necessary.

The inductive telemetry requires the two coils to be closely placed, typically by placing the wand on the body surface over the implantable device. Because the wand is coupled to the programmer using a cable, the inductive telemetry limits the patient's mobility. This limitation is tolerable for patients requiring infrequent routine follow-ups. However, some patients may be very ill or unstable to such an extent that the device is incapable of adjusting itself to provide adequate therapy in a timely manner. Where the patient's condition is life-threatening, telemetry must be active constantly to immediately alert a care provider. Using inductive telemetry would constantly restrain the patient who may otherwise enjoy a more active life.

Alternatively, a far-field radio-frequency (RF) telemetry may substitute for, or supplement to, the inductive telemetry. An RF transceiver in the implantable device is used to communicate with an RF transceiver in the external programmer. With a far-field RF telemetry, the patient is typically free of any body surface attachment that limits mobility. However, RF telemetry typically consumes more energy and requires a larger circuit and battery than inductive telemetry.

Therefore, the present inventors have recognized that there is a need for a method and apparatus to provide an adequate telemetry to an implantable device to satisfy each individual patient's needs without increasing the size and/or the cost of the implantable device.

SUMMARY

An implantable, self-contained, user-attachable or detachable telemetry module plugs into an implantable medical device to provide or supplement one or more telemetry functions needed by a patient having certain health conditions. A user-attachable or detachable telemetry module allows a user, such as a physician or other care provider, to select a telemetry module and attach it to a medical device. Various types of telemetry are implemented as various user-attachable or detachable telemetry modules, each providing one or more telemetry functions suitable for a patient whose particular condition imposes particular demands on telemetry. A care provider selects a user-attachable or detachable telemetry module suitable for each individual patient wearing an implantable medical device. This eliminates a need for implantable medical devices having one or more built-in telemetry functions that may never be used or, alternatively, a need for many types of implantable medical devices, each including one possible combination of telemetry and therapeutic functions, and thus improves healthcare cost efficiency.

In one example, a user-attachable or detachable telemetry module provides for far-field communications between an implantable medical device and a remote external device, for example, capable of communicating over at least a six-foot range. In one example, the user-attachable or detachable telemetry module includes an antenna including a first end and a second end. An RF module, coupled to the first end of the antenna, includes a transmitter and a receiver. An interface connector, coupled to the second end of the antenna, couples the telemetry module to an implantable medical device. In a further example, the RF module is attached to a device body of the implantable medical device via a snap-on connection. In an alternative example, the antenna has one end coupled to the RF module and a free end. The RF module includes an interface connector that allows the RF module to be attached to the implantable medical device with a plug-in connection. Other aspects of the invention will be apparent on reading the following detailed description and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
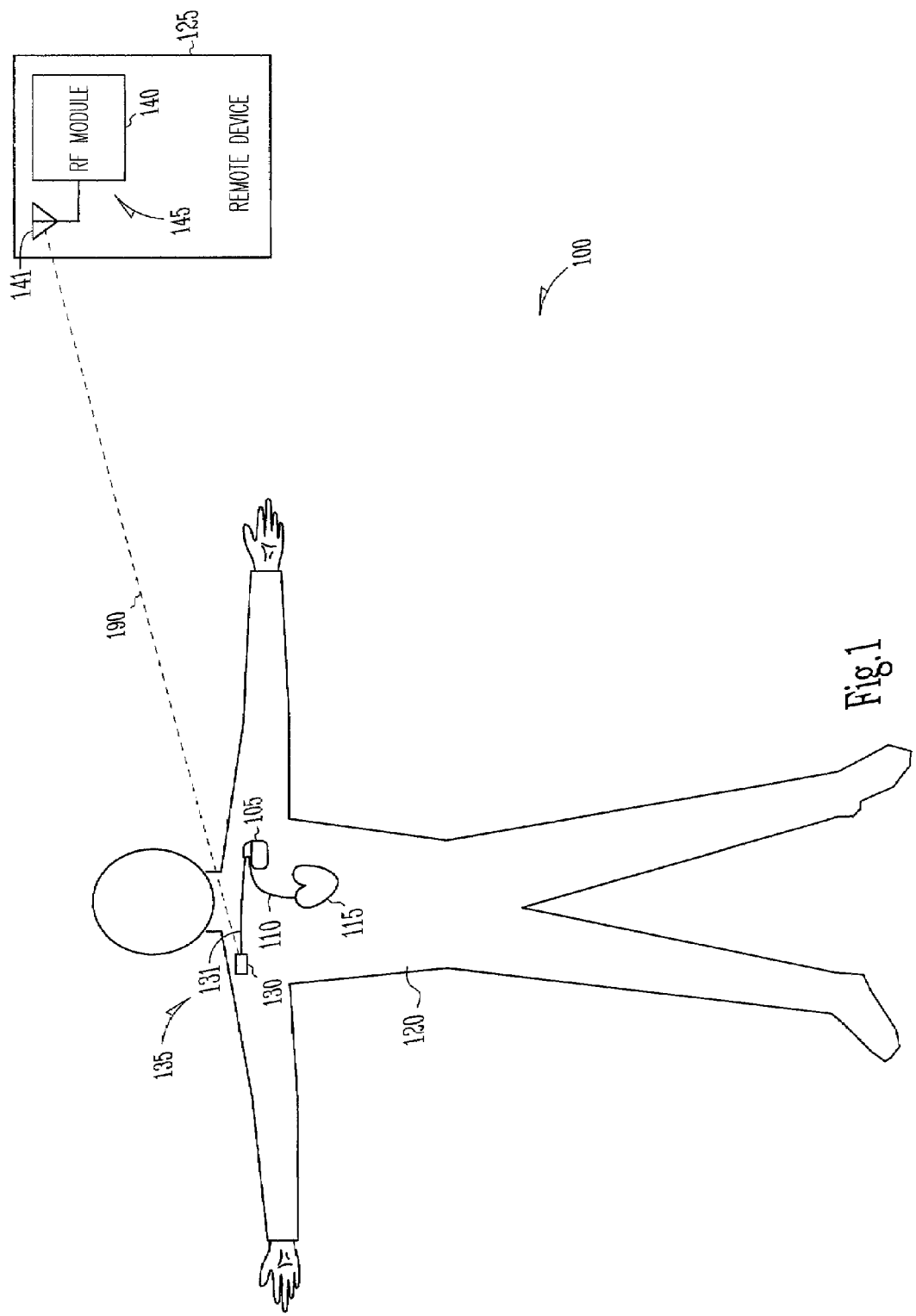
FIG. 1 is a schematic illustration of an example of portions of an implantable system and portions of an environment in which it is used.

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, an implantable, user-attachable or detachable telemetry module connecting to an implantable medical device to provide communication between the implantable device and a remote external device. The present methods and apparatuses will be described in applications involving implantable cardiac rhythm management systems such as pacemakers, CRT devices, cardioverter/defibrillators, and pacer/defibrillators. However, it is understood that the present methods and apparatuses may be employed in other types of implantable medical devices, including, but not being limited to, neurological stimulators, neuromuscular stimulators, drug delivery systems, and various types of physiological signal monitoring devices.

As already discussed, a patient's condition may determine a suitable type of telemetry, in additional to an implantable device having suitable type of therapeutic functions. To minimize size and maximize longevity of the implantable device, the type of telemetry should be selected based on the patient's needs. There is no typical one-to-one correspondence between a suitable type of telemetry and suitable type of therapeutic functions. For example, a patient having a bradyarrhythmia may need a pacer with either inductive telemetry or far-field RF telemetry, depending on whether his condition requires routine follow-ups or frequent monitoring. Similarly, a patient having a tachyarrhythmia may need a defibrillator with either inductive telemetry or far-field RF telemetry. Thus, a patient's condition should determine any possible combination of a suitable type of telemetry and an implantable device having suitable type of therapeutic functions.

It is possible to include two or more types of telemetry in one implantable device. A suitable type of telemetry may be selected by programming the implantable device. This approach allows implantable devices to be categorized by therapeutic function or functions (e.g., pacers, CRT devices, defibrillators, pacer/defibrillators, and drug delivery devices), as they typically are at the present time. However, it is cost inefficient and may result in a device size unsuitable for implantation. Another possibility is to produce implantable devices categorized by predetermined combinations of therapeutic function or functions and telemetry type or types. This approach allows each implantable device to be efficiently used but requires maintenance of an inventory that is cost inefficient and confusing. In addition to cost inefficiency, both approaches have a potential to confuse physicians and other care providers with a complicated device selection and/or programming process.

A user-attachable or detachable telemetry module provides a solution to these problems by allowing a user to select a suitable telemetry device and combine it with an implantable device having suitable type of therapeutic functions. The user-attachable or detachable telemetry module allows a user, such as a physician or other care provider or other person outside the factory that manufactures the implantable device, to select a suitable telemetry module and attach it to a medical device to provide the medical device with telemetry.

FIG. 1 is a schematic illustration of an example of portions of an implantable system 100 and portions of an environment in which it is used. In this example, system 100 is an implantable cardiac rhythm management system including, among other things, an implantable device 105 and a remote external device 125. Implantable device 105 is implanted within a body 120 of a patient and coupled to the patient's heart 115 by a lead system 110. Examples of implantable device 105 include pacemakers, CRT devices, cardioverter/defibrillators, and pacer/defibrillators. Remote external device 125 provides a user interface for system 100. The user interface allows a physician or other care provider to interact with implantable device 105 through a wireless telemetry link 190. Telemetry link 190 provides for communications between implantable device 105 and remote external device 125. In one example, telemetry link 190 provides for bi-directional communications between implantable device 105 and remote external device 125. In another example, telemetry link 190 provides for uni-directional communications from implantable device 105 to remote external device 125. In an alternative example, telemetry link 190 provides for uni-directional communications from remote external device 125 to implantable device 105. In the example of FIG. 1, telemetry link 190 is provided by an external telemetry module 145 within or coupled to remote external device 125 and an implantable telemetry module 135 coupled to implantable device 105. In one example, implantable telemetry module 135 is coupled to implantable device 105 (for example, outside the facility that manufactures the implantable device 105) using a user-attachable connector, and is therefore referred to as a user-attachable telemetry module. In one example, implantable telemetry module 135 is coupled to implantable device 105 (e.g., at the factory or elsewhere) using a detachable connector, and is therefore referred to as a detachable telemetry module.

External telemetry module 145 includes, among other things, an external RF module 140 and an antenna 141. In one example, antenna 141 is a quarter-wavelength antenna suitable for far-field telemetry. External RF module 140 includes a transmitter and a receiver. The transmitter generates an RF carrier signal and modulates it with data being transmitted, such as to implantable device 105. The modulated signal is amplified by an amplifier and emitted though antenna 141. The receiver receives through antenna 141 a modulated RF signal, such as from implanted user-attachable or detachable telemetry module 135 and demodulates the signal to recover data transferred from implantable device 105.

Implanted user-attachable or detachable telemetry module 135 includes, among other things, an RF module 130 and a lead 131. In one example, lead 131 carries an antenna, such as a quarter-wavelength antenna suitable for far-field telemetry. RF module 130 includes a transmitter and a receiver. The transmitter generates an RF carrier signal and modulates it with data being transmitted to remote external device 125. The modulated signal is amplified by an amplifier and emitted though the antenna. The receiver receives, through the antenna, a modulated RF signal coming from external telemetry module 145 and demodulates the signal to recover data transferred from remote external device 125.

In one example, telemetry link 190 is a far-field telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of far-field telemetry link 190 (a distance over which data is capable of being wirelessly communicated) is at least six feet but can be as long as allowed by the particular communication technology. Unlike a near-field inductive telemetry link using a wand close to device 105 and electrically connected to remote external device 125, using the far-field telemetry link of this example, no cable from body 120 to external telemetry module 145 is needed.

User-attachable or detachable telemetry module 135 includes one or more user15 attachable connectors to allow physical and electrical connection to implantable device 105. In one example, the user-attachable connectors are detachable after attachment. In the example of FIG. 1, the one or more user-attachable or detachable connectors are coupled to one end of lead 131. RF module 130 is coupled to the other end of lead 131. A physician determines therapeutic and telemetry functions suitable for a particular patient and accordingly selects a particular type of implantable device 105 from among a plurality of types and a particular type of user-attachable or detachable telemetry module 135 among a plurality of types. In one example, user-attachable telemetry module 135 is coupled to implantable device 105 before or during an implantation operation. In another example, user-attachable telemetry module 135 is coupled to implantable device 105 in a manufacturing or assembly site, however, it is configured to be capable of being attached by a user outside the manufacturing facility.

Figure 2:
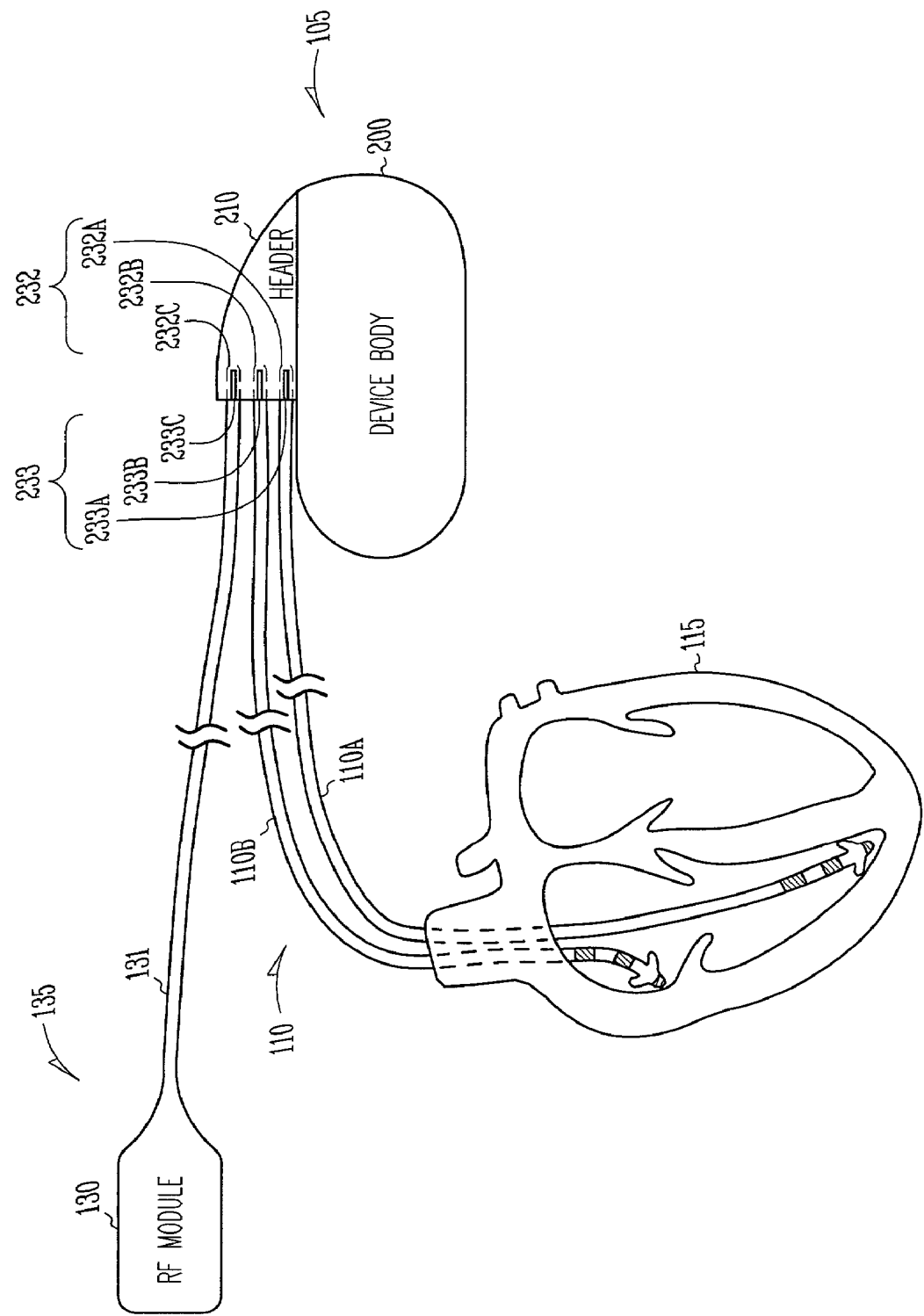
FIG. 2 is a schematic illustration of an example of a remote user-attachable or detachable telemetry module coupled to an implantable device by a lead.

FIG. 2 is a schematic illustration of an example of user-attachable or detachable telemetry module 135 coupled to implantable device 105. In this example, implantable device 105 is an implantable cardiac rhythm management device such as a pacer, a CRT device, a cardioverter/defibrillator, or a pacer/defibrillator. Lead system 110, including leads 110A and 110B, couples implantable device 105 to heart 115 to allow monitoring of electrical signals from heart 115 and delivering electrical stimulation to heart 115. User-attachable or detachable telemetry module 135 provides telemetry for implantable device 105.

Implantable device 105 includes a device body 200 and a header 210. Device body 200 includes a pulse generator having an energy source, such as one or more batteries, and an electronic circuit. In this example, the pulse generator is contained within a metal housing ("can") and hermetically sealed, with wire feedthroughs allowing access to outside of the can. Header 210 is permanently attached to device body 200 and includes the wire feedthroughs and one or more electromechanical connectors 232. In the example of FIG. 2, implantable device 105 is coupled to two regions of heart 115 by two leads, 110A and 110B. Header 210 includes two lead connectors 232A and 232B for mechanically securing lead system 110A and 110B into implantable device 105 and electrically coupling these leads to the electronic circuit within the can. One example of lead connectors 232A and 232B, each including a socket into which a lead having a conducting pin terminal (shown as 233A/233B) is inserted, is discussed in Bradshaw et al. U.S. Pat. No. 5,545,188 ("the Bradshaw patent"), entitled "CARDIAC PACEMAKERS WITH COLLET-TYPE LEAD CONNECTOR," assigned to Intermedics, Inc., which is incorporated herein by reference in its entirety.

In the example of FIG. 2, header 210 further includes at least one connector 232C into which a mating portion of user-attachable or detachable telemetry module 135 is plugged into implantable device 105. Connector 232C also provides for electrical coupling between user-attachable or detachable telemetry module 135 and the electronic circuit of implantable device 105. Using this electrical connection, data is communicated from header 210 to user-attachable or detachable telemetry module 135, and vice versa. One suitable example of connectors 232C and 233C is discussed in the Bradshaw patent.

In the example of FIG. 2, user-attachable or detachable telemetry module 135 includes RF module 130 and lead 131. RF module 130 includes a far-field RF telemetry circuit. In one example, the far-field RF telemetry circuit is capable of wirelessly transmitting and receiving data over a range of at least six feet. The telemetry circuit is contained within a hermetically sealed housing, with wire feedthroughs allowing electrical connection between RF module 130 and lead 131. Lead 131 carries, among other things, an antenna that provides for RF signal emission and reception. Lead 131 also provides electrical and mechanical coupling between RF module 130 and implantable device 105. In this example, lead 131 extends from RF module 130 and terminates at male connector 233C, which is plugged into female connector 232C.

In one example, after selecting a combination of a particular type of implantable device 105 and a particular type of user-attachable or detachable telemetry module 135 suitable for a patient, user-attachable or detachable telemetry module 135 is coupled to implantable device 105 using matching connectors 233C and 232C before or during implantation. In another example, a suitable combination of one type of implantable device 105 and one type of user-attachable or detachable telemetry module 135, pre-assembled in a manufacturing or assembly site, is selected for the patient before implantation. In one example, if a different type of telemetry is desired after implantation, user-attachable or detachable telemetry module 135 can be detached from implantable device 105 by separating connectors 233C and 232C. A different user-attachable or detachable telemetry module 135 can then be coupled to implantable device 105, which need not be replaced.

Figure 3:
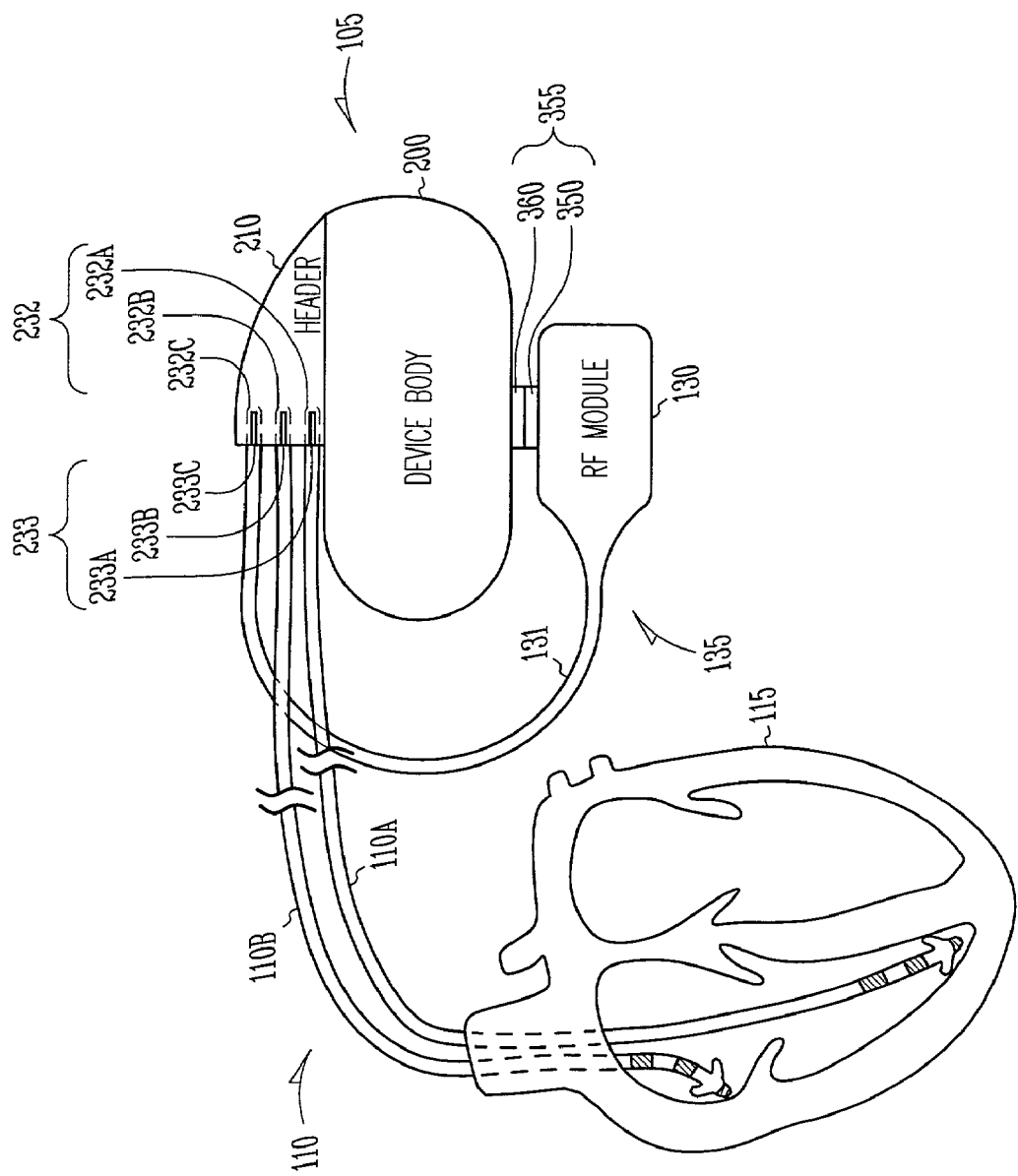
FIG. 3 is a schematic illustration of an example of a proximal user-attachable or detachable telemetry module coupled to an implantable device by a lead.

FIG. 3 is a schematic illustration of an alternative example of user-attachable or detachable telemetry module 135 coupled to implantable device 105. In this example, an additional mechanical fixture 355 physically attaches RF module 130 onto implantable device 105. In one example, mechanical fixture 355 includes one or more screws to unite components 360 and 350, respectively attached to device body 200 and RF module 130. In another example, mechanical fixture 355 includes two snap-on components 360 and 350. In a further example, the snap-on connection is reinforced with one or more screws.

Fixing RF module 135 onto device body 105 provides control over the physical placement of lead 131. This obtains consistent orientation of the antenna in lead 131, in relation to each patient's implantable device 105. This may also prevent implantable device 105 from acting as a shield attenuating the RF signals transceived by the antenna in lead 131. Mechanical fixture 355 may also provide for an electrical connection between the housings of device body 200 and RF module 130, thus forming a common electrical ground, if desired. In an alternative example, components 360 and 350 include wire feedthroughs allowing access to the electronic circuit within device body 200 and RF module 130, respectively. Components 360 and 350 also include conductive pins and/or receptacles such that mechanical fixture 355 also allows for electrical connection, in addition to mechanical connection, between implantable device 105 and RF module 130.

Figure 4A:
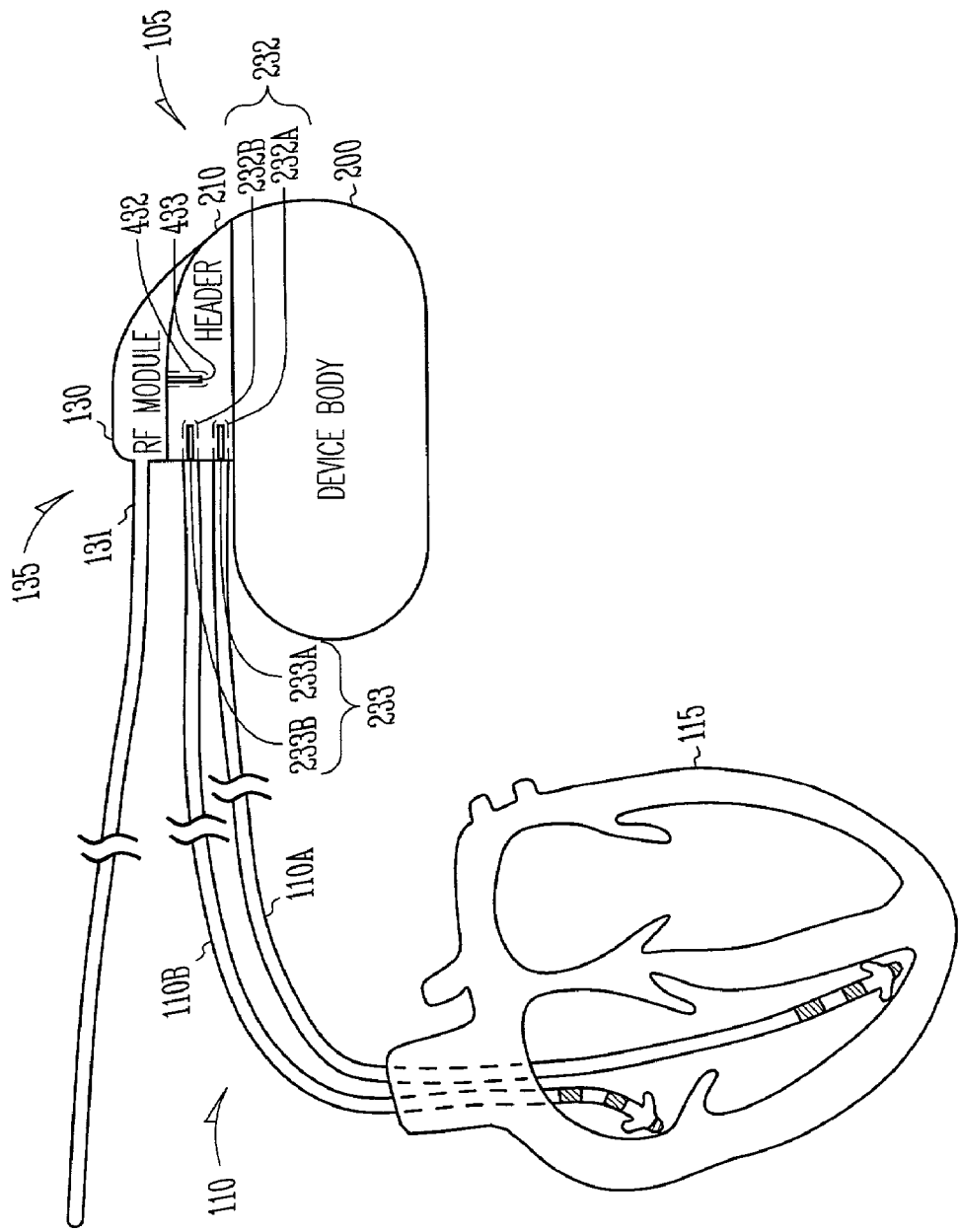
FIG. 4A is a schematic illustration of an example of a proximal user-attachable or detachable telemetry module, coupled to an implantable device, with an outwardly extending antenna-carrying lead.

FIGS. 4A, 4B, 4C, and 4D are schematic illustrations of yet another example of user-attachable or detachable telemetry module 135 coupled to implantable device 105. In the example illustrated in FIG. 4A, RF module 130 physically attaches onto header 210, such as by using at least one pair of plug-in connectors 432 and 433, which are associated with header 210 and RF module 130, respectively. Lead 131 extends from RF module 130 and carries the antenna. In the example of FIG. 4A, the antenna includes an elongated conductor. Alternative examples of the antenna include a monopole antenna, a dipole antenna, a patch antenna, and a slot antenna.

Connectors 432 and 433 include one or more pins and the same number of corresponding receptacles to allow user-attachable or detachable telemetry module 135 to be connected to and disconnected from implantable device 105 as needed. Additional features, such as one or more screws, may be used to provide or reinforce the connection provided by connectors 432 and 433.

Figure 4B:
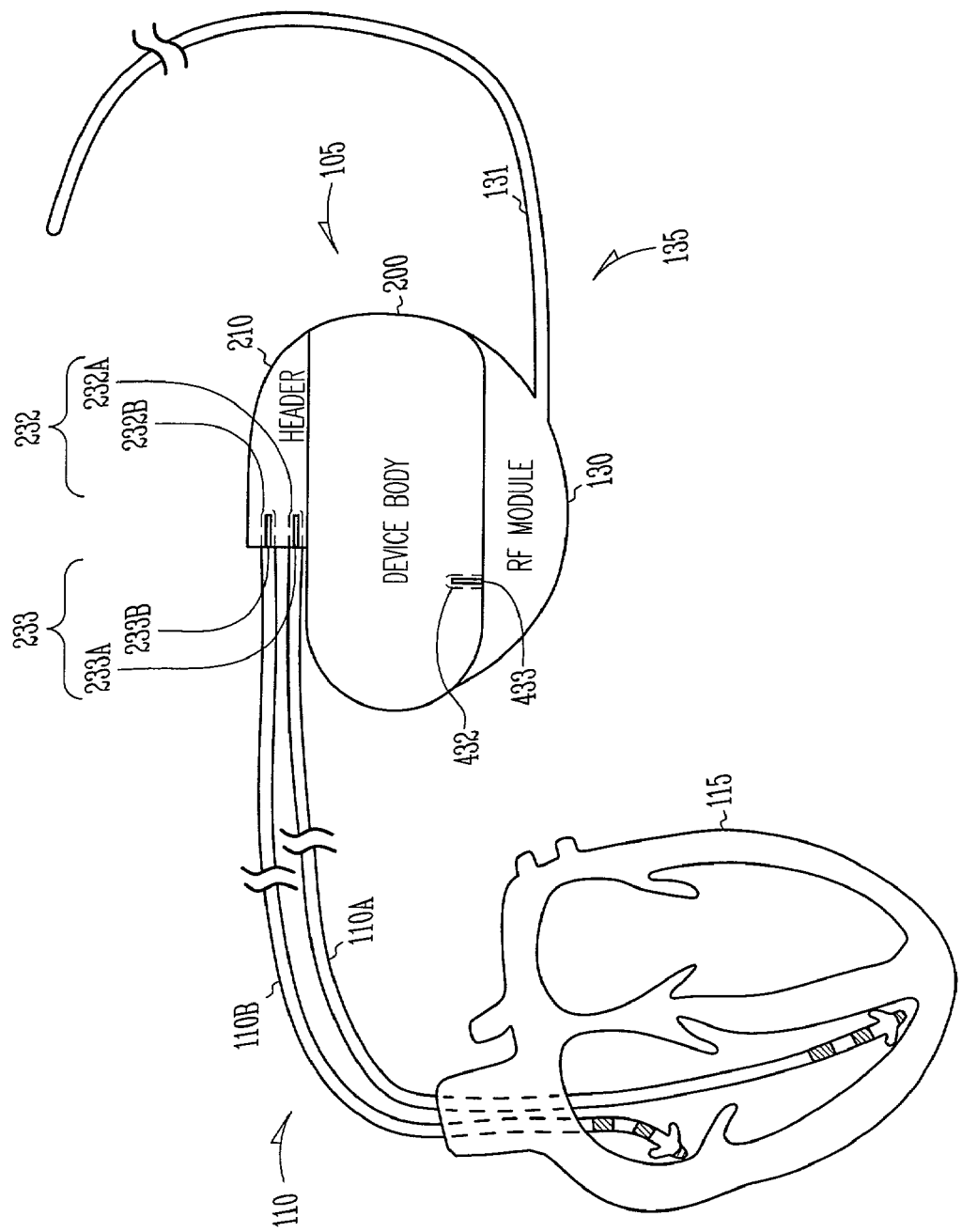
FIG. 4B is a schematic illustration of another example of a proximal user-attachable or detachable telemetry module, coupled to an implantable device, with an outwardly extending antenna-carrying lead.

In an alternative example illustrated in FIG. 4B, connector 432 is included in device body 200. RF module 130 physically attaches onto device body 200.

Figure 4C:
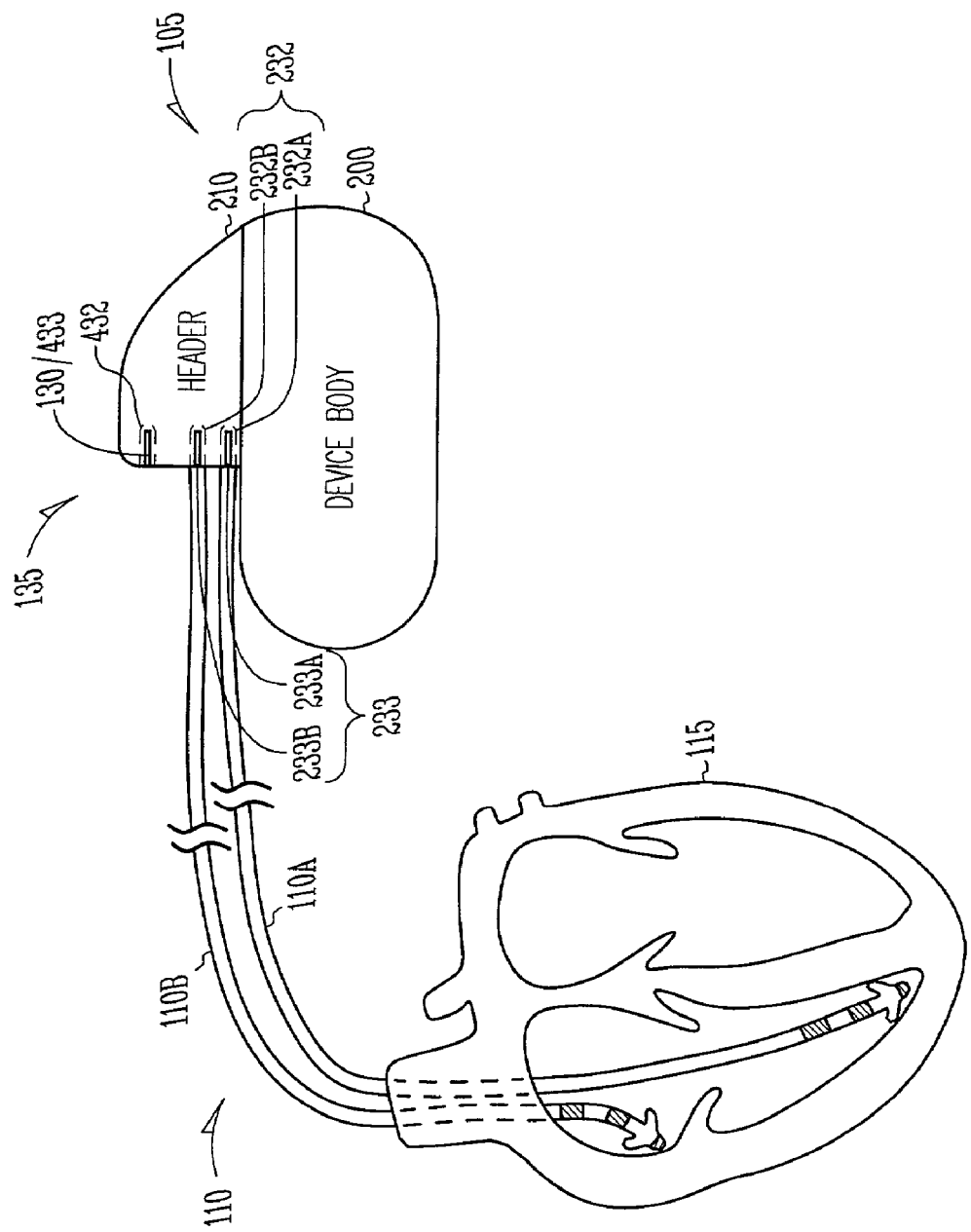
FIG. 4C is a schematic illustration of one example of a proximal user-attachable or detachable telemetry module within a connector plugged into an implantable device.

In another alternative example illustrated in FIG. 4C, RF module 130 and the antenna are both constructed entirely within connector 433. In one example, one or more set screws are used to provide or reinforce the connection between connectors 432 and 433. In an additional example, the one or more set screws are also used to provide electrical connection(s) for power and/or data transmission between RF module 130 and device body 200 provided for by connectors 432 and 433.

Figure 4D:
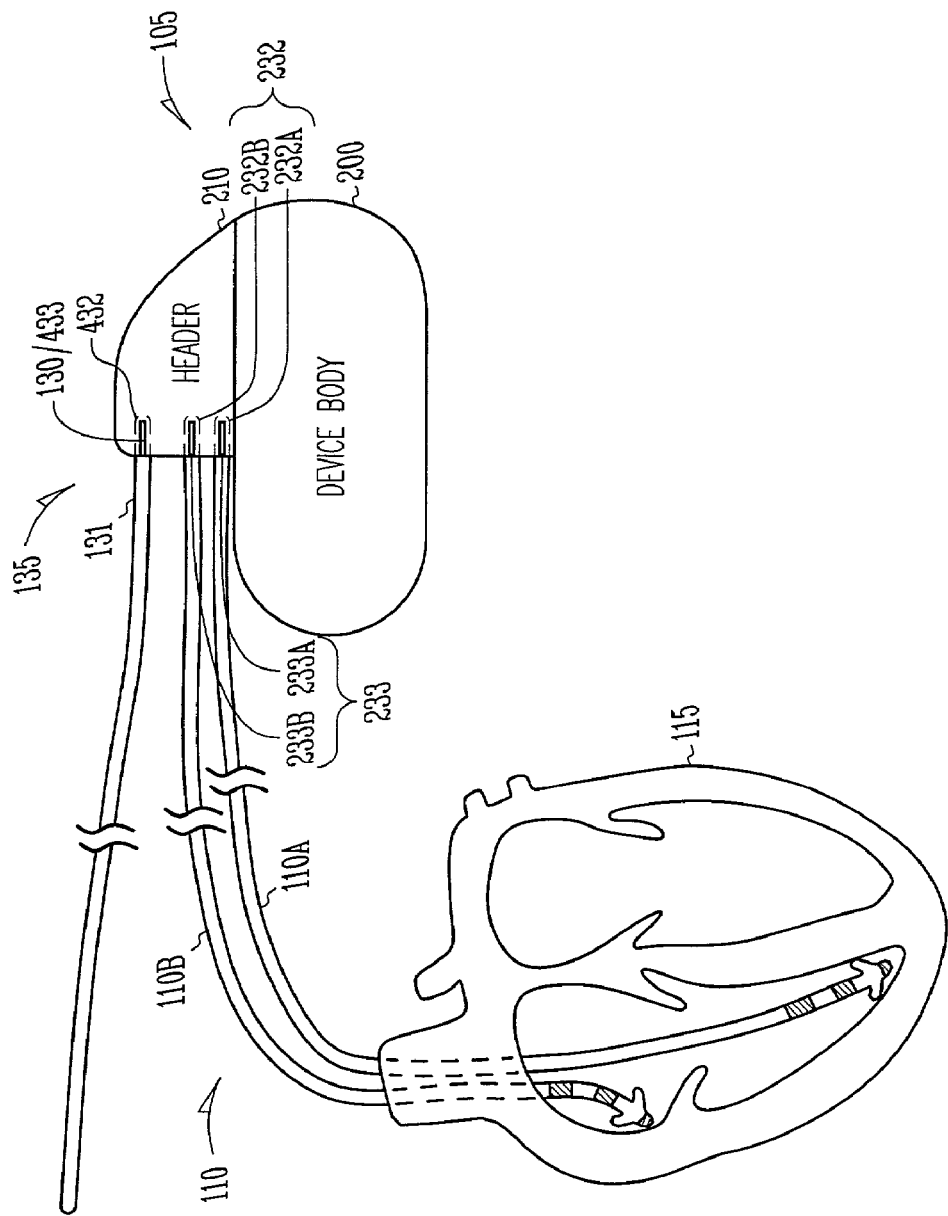
FIG. 4D is a schematic illustration of one example of a proximal user-attachable or detachable telemetry module within a connector, plugged into an implantable device, with an outwardly extending antenna-carrying lead.

In another alternative example illustrated in FIG. 4D, RF module 130 is constructed entirely within connector 433. Lead 131 extends from RF module 130 and carries the antenna.

In a further example, if a different type of telemetry is desired after implantation, user-attachable or detachable telemetry module 135 can be detached from implantable device 105 by separating connectors 433 and 432. A different user-attachable or detachable telemetry module 135 can then be coupled to implantable device 105, which need not be replaced.

Figure 5:
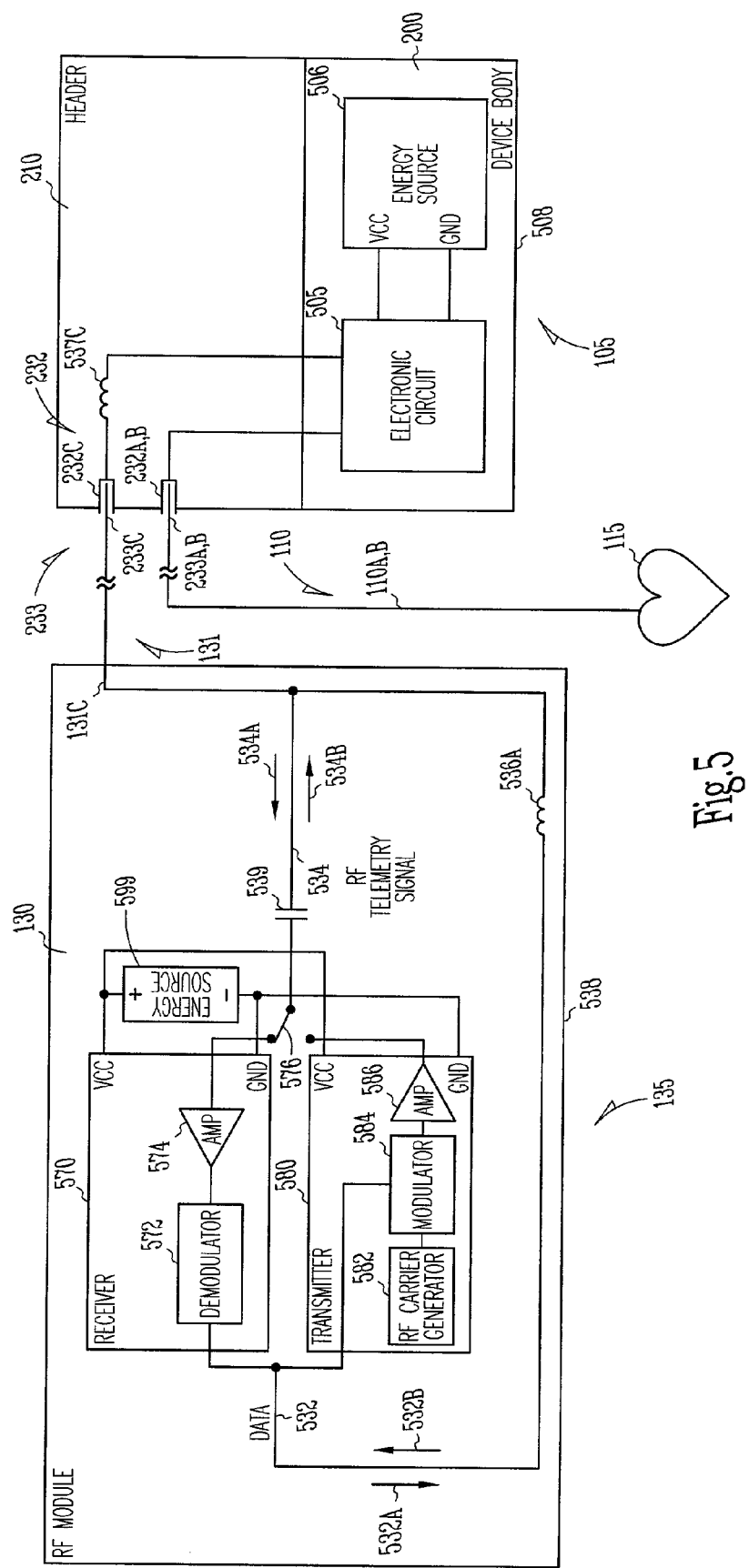
FIG. 5 is a schematic/block diagram showing an example of a circuit of a user-attachable or detachable telemetry module coupled to an implantable device, such as shown in FIGS. 2 and 3.

FIG. 5 is a schematic/block diagram showing an example of a circuit of user-attachable or detachable telemetry module 135 electrically and mechanically coupled to implantable device 105 by connectors 232C and 233C. In this example, implantable device 105 is an implantable cardiac rhythm management device including device body 200 and header 210. Header 210 is permanently attached to device body 200. Device body 200 includes an electronic circuit 505 and an energy source 506, coupled to circuit 505, to provide circuit 505 with power required for its operation. Device body 200 is housed in a conductive housing 508 and hermetically sealed. Housing 508 is exposed to body tissue after the implantation. Energy source 506 includes one or more batteries. Circuit 505, electrically coupled to heart 115 through lead system 110 and header 210, includes functional modules that monitors physiological activities of a patient and delivers one or more types of therapy to heart 115 of the patient through lead system 110. Such functional modules are known in the art of cardiac rhythm management using implantable devices. Examples of such functional modules are discussed in Langer et al. U.S. Pat. No. 4,407,288, entitled "IMPLANTABLE HEART STIMULATOR AND STIMULATION METHOD," assigned to Mieczyslaw Mirowski, which is incorporated herein by reference in its entirety.

In the example shown in FIG. 5, lead system 110 includes leads 110A and 110B, each including two ends. One end is coupled to one or more electrodes in contact with heart 115. The other end is coupled to a conductive pin connector, 233A or 233B, which is inserted into a corresponding receptacle connector, 232A or 232B, of header 210. In this way, an electrical continuity is formed between heart 115 and circuit 505.

Circuit 505 is programmed to provide one or more monitoring and/or therapeutic functions suitable for each individual patient. User-attachable or detachable telemetry module 135 provides one means of programming circuit 505 by sending it commands and parameters. Each command causes circuit 505 to perform one or more functions. Examples of such functions include acquiring physiological data, performing at least one self-diagnostic test for a device operational status, and/or delivering at least one therapy. The parameters are required to define and control how each function is performed. For example, if the function is to deliver a pacing therapy, the parameters may include, among other things, a pacing mode, a maximum pacing rate, a minimum pacing rate, and values needed to quantitatively define a stimulus waveform.

User-attachable or detachable telemetry module 135 transfers data from circuit 505 to remote device 125. This may include, for example, transmitting real-time physiological data acquired by circuit 505, extracting physiological data acquired by and stored in circuit 505, extracting therapy history data stored in circuit 505, and extracting data indicating an operational status of circuit 505.

In one example, circuit 505 includes a telemetry circuit that is independent from that in user-attachable or detachable telemetry module 135. For example, circuit 505 may include an inductive telemetry circuit providing for near-field telemetry used in regularly scheduled routine follow-ups in a physician's office, and user-attachable or detachable telemetry module 135 provides for far-field telemetry for communicating over a long distance, such as notifying a physician of an urgent situation for a patient who is at home. Alternatively, user-attachable or detachable telemetry module 135 exclusively provides all telemetry for implantable device 105.

In the example shown in FIG. 5, user-attachable or detachable telemetry module 135 includes RF module 130 and lead 131. RF module 130 includes an energy source 599, a receiver 570, and a transmitter 580. In one example, RF module 130 is housed in a conductive housing 538 and hermetically sealed. Housing 538 is exposed to body tissue after the implantation. Energy source 599 includes one or more batteries and supplies power to receiver 570 and transmitter 580. Receiver 570 includes an amplifier 574 and a demodulator 572. Amplifier 574 includes an input that is coupled to an antenna 131C, carried in lead 131, through a capacitor 539 that decouples a dc component of RF telemetry signal 534 and a transmitter/receiver switch (TR switch) 576. Signal 534 includes either an incoming signal 534A that is to be received or an outgoing signal 534B that is transmitted by the user-attachable or detachable telemetry module 135. Signal 534A is amplified by amplifier 574 and demodulated by demodulator 572 to result in an incoming component 532A of binary data 532. In one example, signal 534A is an RF signal amplitude-modulated with binary data, and demodulator 572 is an envelope detector. In an alternative example, signal 534A is an RF signal frequency-modulated with binary data, and demodulator 572 is frequency demodulator. In another alternative example, signal 534A is an RF signal phase-modulated with binary data, and demodulator 572 is a phase demodulator. Data 532A is passed to the implantable device 105 by using antenna 131 C, which also functions as a conductor providing for wired data transmission between RF module 130 and implantable device 105. An RF choke (RFC) 536A, between the output of demodulator 572 and antenna 131 C, prevents RF telemetry signal 534 and any noise received by antenna 131C from interfering with the operation of RF module 130.

Transmitter 580 includes an RF carrier generator 582, a modulator 584, and an amplifier 586. RF carrier generator 582 includes an oscillator generating a carrier signal for far-field data transmission, such as over a telemetry range of at least six feet. Modulator 584 includes a carrier input coupled to the output of RF carrier generator, and a signal input electrically connected to implantable device 105 through the wire of antenna 131C and through RFC 536A. Data 532 includes an outgoing component 532B that is conducted from implantable device 105 via a wired connection. In one example, modulator 584 is an amplitude modulator by which the RF carrier is modulated by data 532B to result in an amplitude-shift keyed RF signal. In an alternative example, modulator 584 is a frequency modulator by which the RF carrier is modulated by data 532B to result in a frequency-shift keyed RF signal. In another alternative example, modulator 584 is a phase modulator by which the RF carrier is modulated by data 532B to result in a phase-shift keyed RF signal. The modulator outputs a modulated RF signal that is amplified by amplifier 586 to result in signal 534B, which is transmitted to, through capacitor 539 and TR switch 576, antenna 131C and emitted from antenna 131C.

In one example, telemetry link 190 allows data transmission in two directions (e.g., from external remote device 125 to implantable device 105, and from implantable device 105 to external remote device 125) using time-sharing coordinated with a handshake or other protocol. In one example, data is transmitted in one direction at a time over telemetry link 190, controlled by TR switch 576. In a first state, TR switch 576 couples receiver 570 to antenna 131 C to allow data transmission from external remote device 125 to implantable device 105. In a second state, TR switch 576 couples transmitter 580 to antenna 131C to allow data transmission from implantable device 105 to external device 125.

Implantable device 105 includes RFC 537C, between connector 232C and circuit 505, to prevent RF telemetry signal 534 and any noise received by antenna 131C from interfering with operation of circuit 505.

Figure 6A:
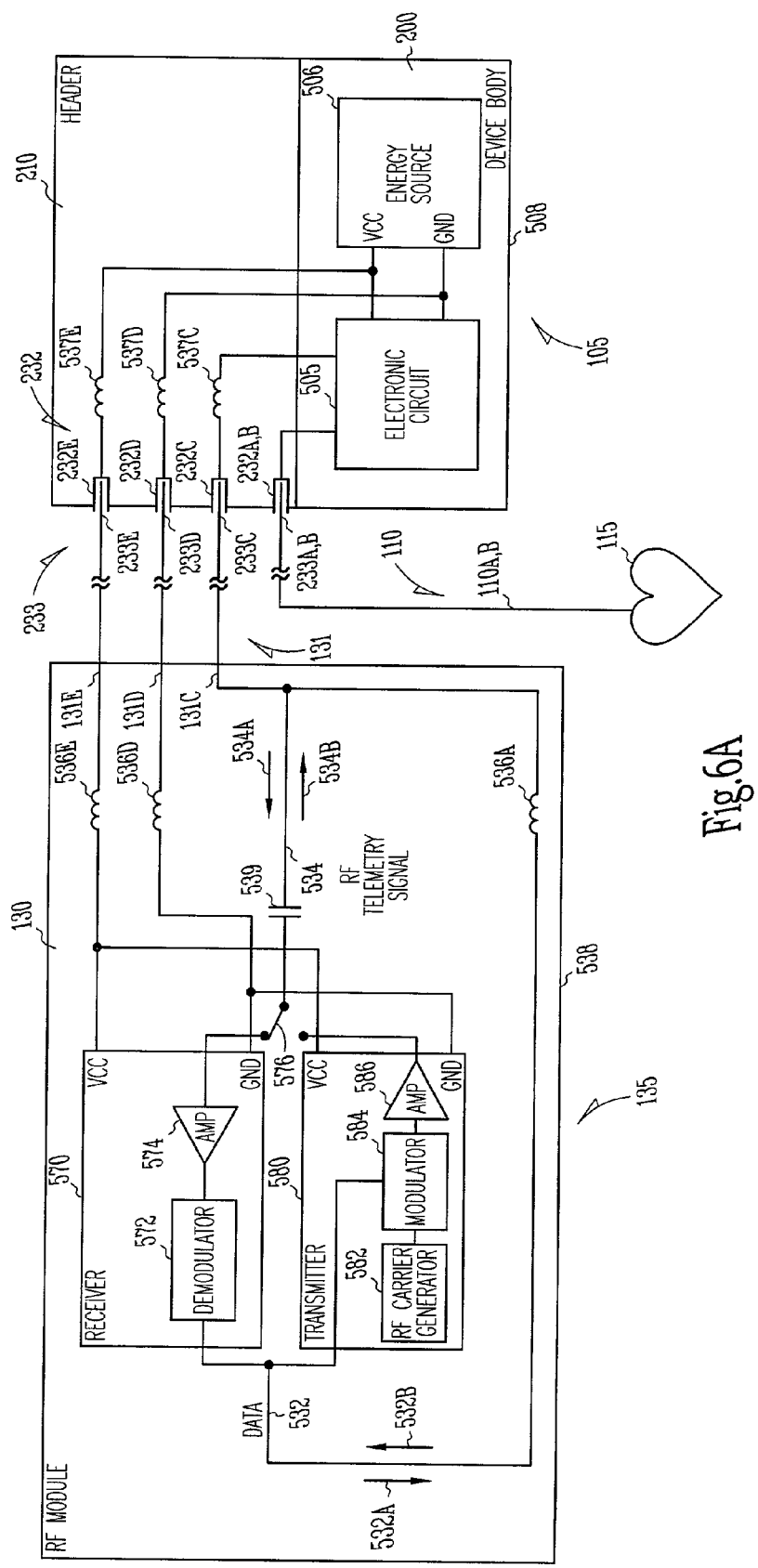
FIG. 6A is a schematic/block diagram showing an alternative example of a circuit of the user-attachable or detachable telemetry module coupled to an implantable device, such as shown in FIGS. 2 and 3.
Figure 6B:
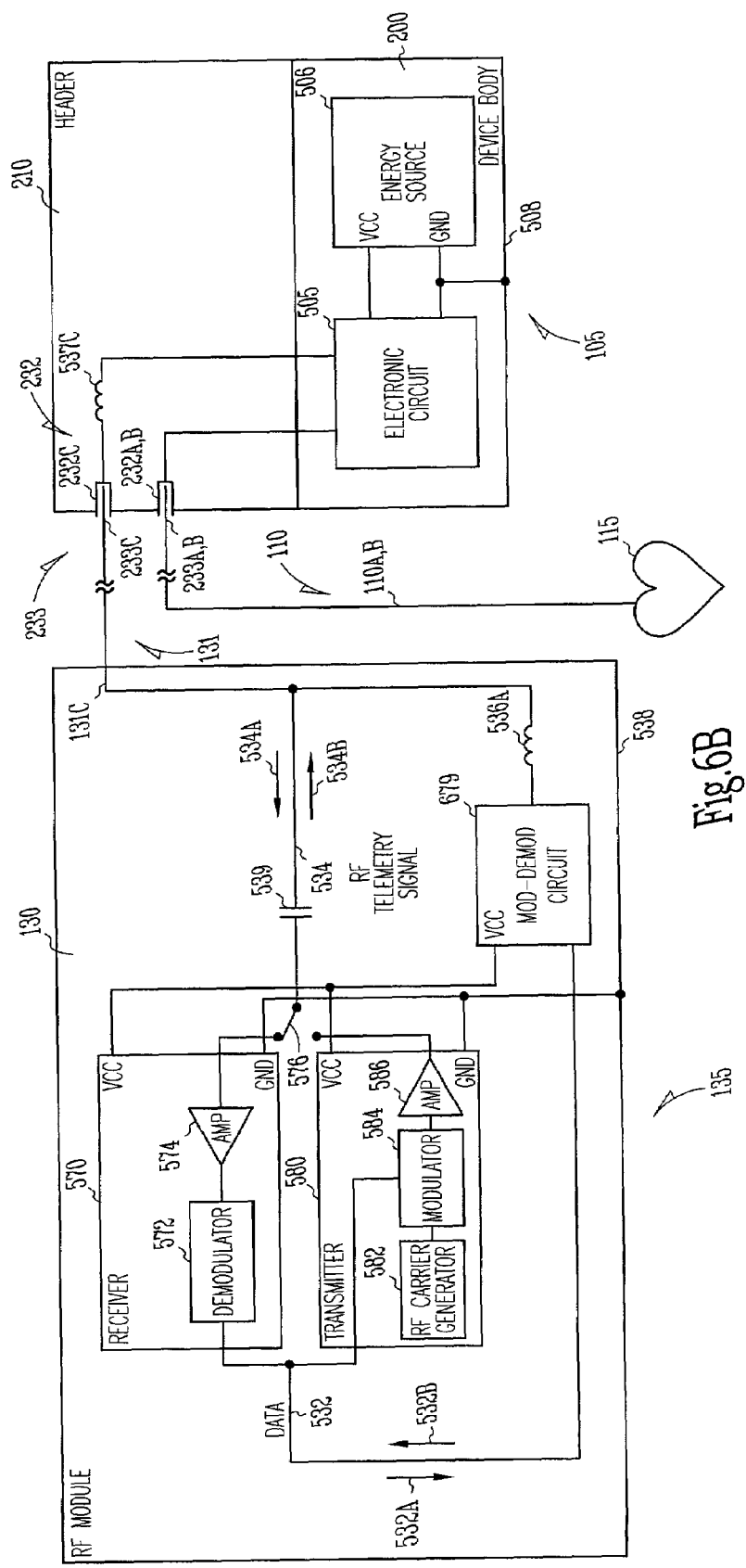
FIG. 6B is a schematic/block diagram showing another alternative example of a circuit of the user-attachable or detachable telemetry module coupled to an implantable device, such as shown in FIGS. 2 and 3.

FIGS. 6A and 6B are schematic/block diagrams showing an alternative example of a circuit of user-attachable or detachable telemetry module 135 coupled to implantable device 105, in which RF module 130 does not include an energy source, but is instead energized by energy source 506 within implantable device 105. In the example illustrated in FIG. 6A, in addition to antenna 131 C, lead 131 also carries conductors 131D and 131E for energy transmission. RF module 130 is coupled to conductors 131D and 131E through RFCs 536D and 536E, which prevent RF energy present in lead 131 from interfering with operation of RF module 130. In this example, additional connector pairs 232D–233D and 232E–233E are used to couple conductors 131D and 131E, respectively, to energy source 506, through header 210. RFCs 537D and 537E are placed between connector 232D and 232E, respectively, and energy source 506 to prevent RF energy present in lead 131 from interfering with operation of circuit 505.

In the example illustrated in FIG. 6B, lead 131 carries only antenna 131 C that is also utilized for transmitting data 532 between user-attachable or detachable telemetry module 135 and implantable device 105 and for transmitting power VCC from implantable device 105 to user-attachable or detachable telemetry module 135. In this example, RF module 130 further includes a VCC modulation-demodulation circuit 679. To transmit data 532B from implantable device 105 to user-attachable or detachable telemetry module 135 via conductor 131C, circuit 505 modulates VCC with data 532B. Circuit 679 demodulates the data-modulated VCC to recover both data 532B and VCC. Housing 508 of device body 200 is connected to a circuit ground of device body 200. Housing 538 of RF module 130 is connected to a circuit ground of RF module 130. To transmit data 532A from user-attachable or detachable telemetry module 135 to implantable device 105, circuit 679 modulates VCC with data 532A. Circuit 505 demodulates the data-modulated VCC to recover data 532A. Housing 508 and housing 538 form a common ground through body tissue for closing a loop of the power transmission. In one example, VCC is amplitude modulated by either data 532A or 532B. Circuit 679 includes a low-pass filter and a voltage regulator to recover VCC. In a further example, VCC is on-off modulated by either data 532A or 532B.

Figure 7:
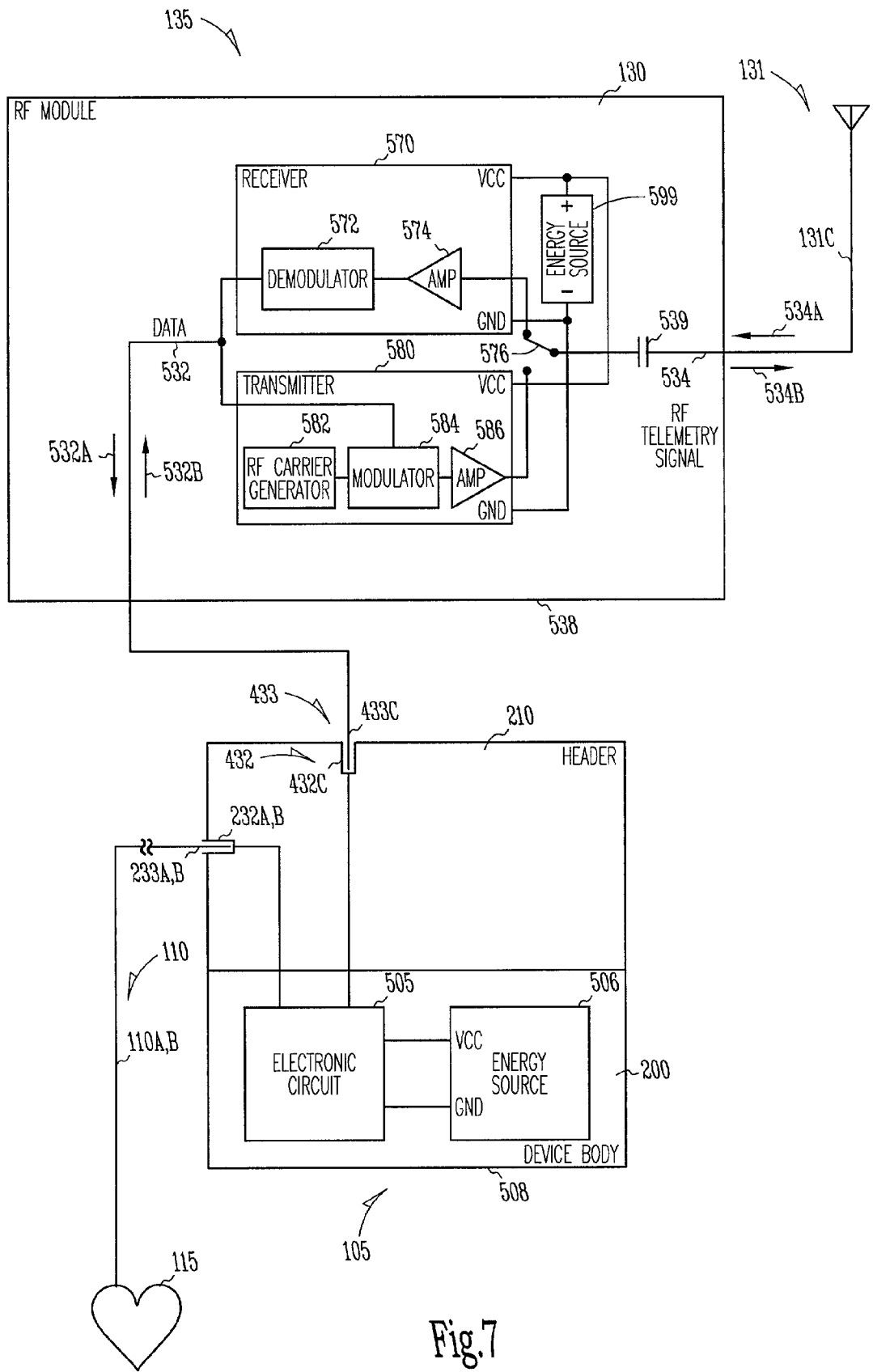
FIG. 7 is a schematic/block diagram showing an example of a circuit of the user-attachable or detachable telemetry module coupled to an implantable device, such as shown in FIG. 4.

FIG. 7 is a schematic/block diagram showing an example of a circuit of user-attachable or detachable telemetry module 135 coupled to implantable device 105, in which RF module 130 directly plugs into header 210 through a pair of connectors 432 and 433. Connector pair 432–433 include connector pair 432C and 433C to provide for electrical connection allowing data 532 to flow between RF module 130 and circuit 505. Lead 131 carries antenna 131 C and extends from RF module 130, but is not directly coupled to implantable device 105.

Figure 8A:
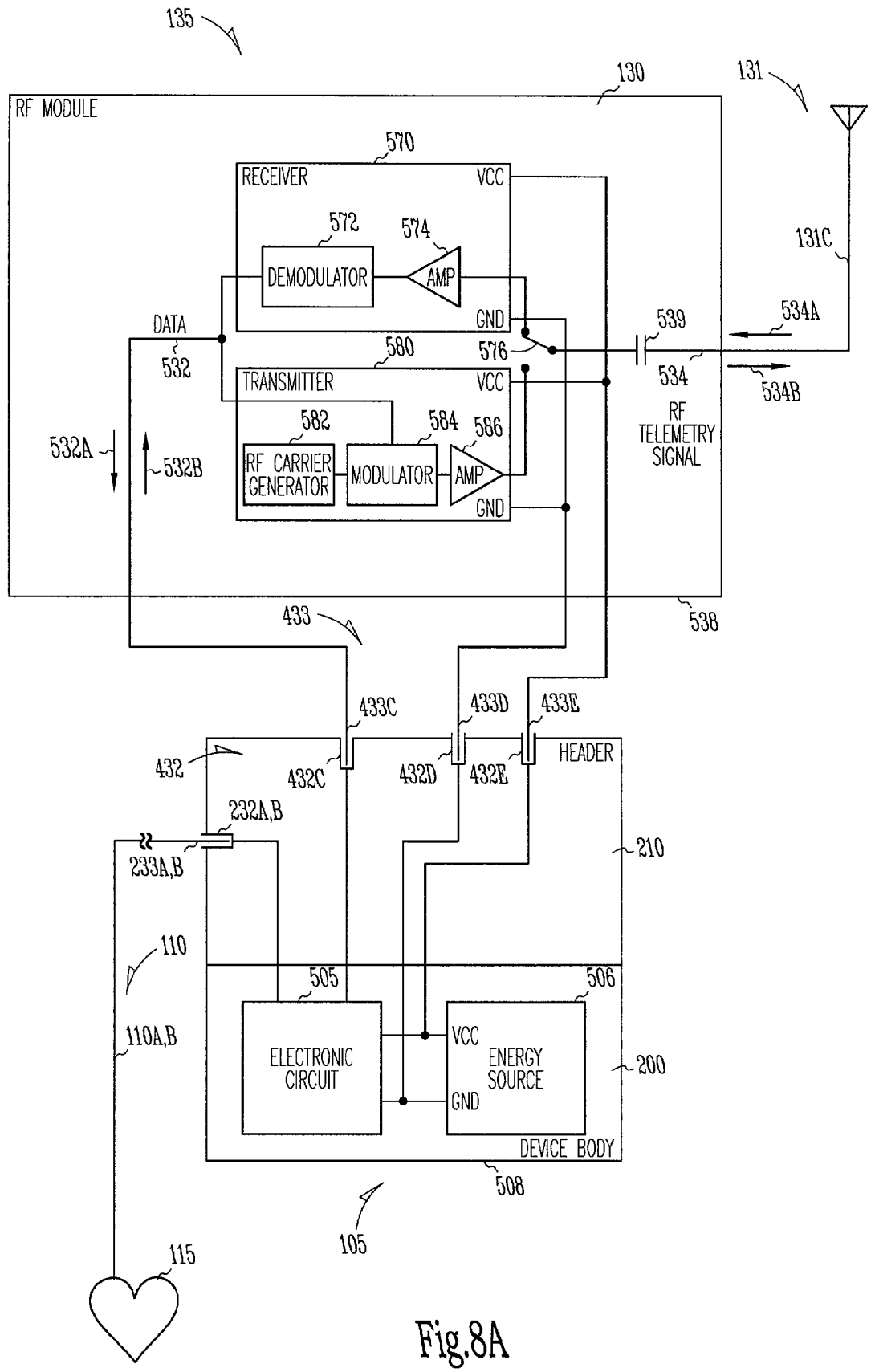
FIG. 8A is a schematic/block diagram showing an alternative example of a circuit of the user-attachable or detachable telemetry module coupled to an implantable device, such as shown in FIG. 4.
Figure 8B:
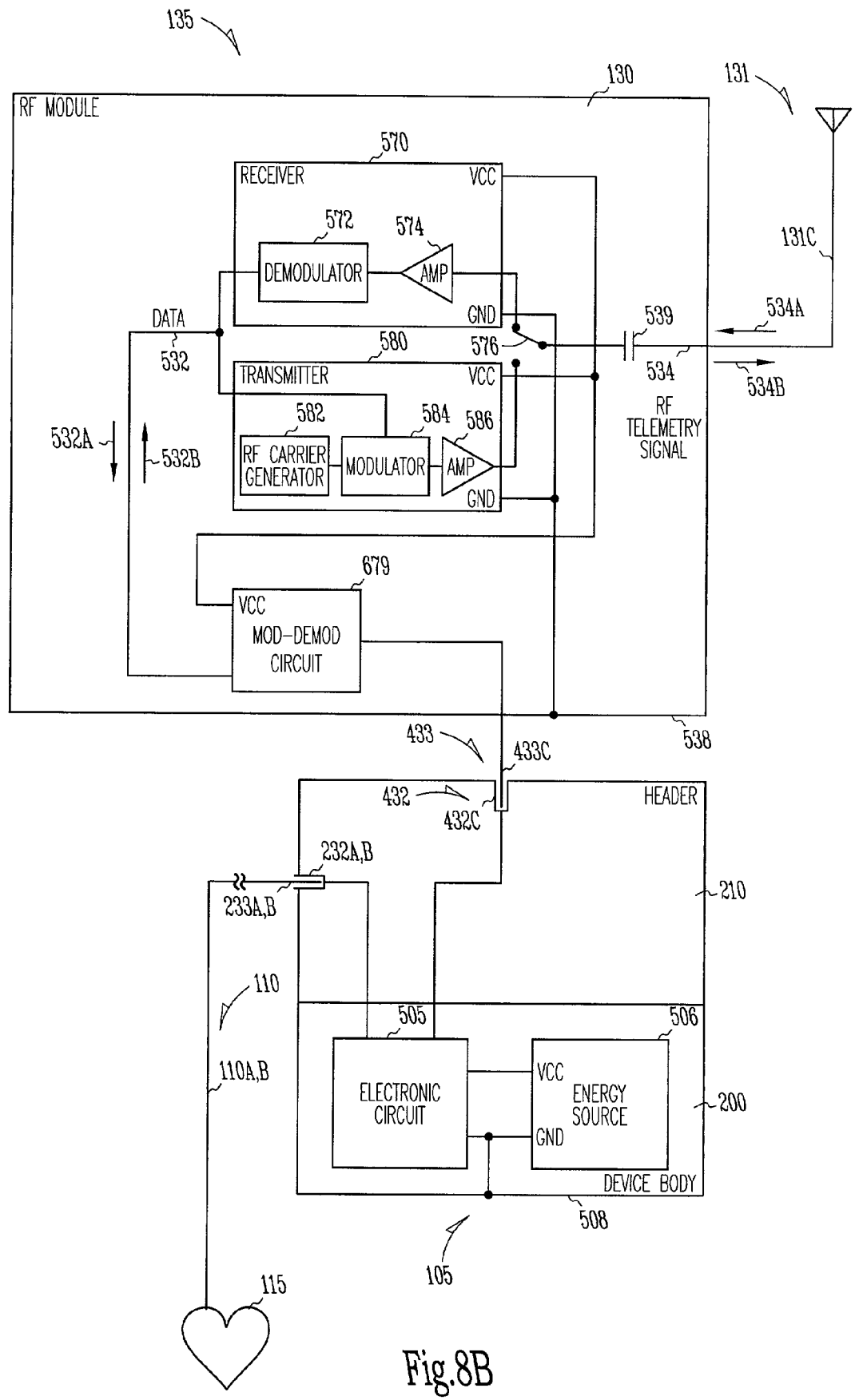
FIG. 8B is a schematic/block diagram showing another alternative example of a circuit of the user-attachable or detachable telemetry module coupled to an implantable device, such as shown in FIG. 4.

FIGS. 8A and 8B are a schematic/block diagrams showing an alternative example of a circuit of user-attachable or detachable telemetry module 135 coupled to implantable device 105, in which RF module 130 directly plugs into header 210 through a pair of connectors 432 and 433. In the example illustrated in FIG. 8A, connectors pair 432–433 includes connector pair 432C and 433C, to provide for electrical connection allowing data 532 to flow between RF module 130 and circuit 505, and connector pairs 432D–433D and 432E–433E to allow energy transmission from energy source 506 to RF module 130. Lead 131 still carries antenna 131C and extends from RF module 130, but is not directly coupled to implantable device 105 and does not carries conductors for energy transmission.

In the example illustrated in FIG. 8B, connectors pair 432–433 includes connector pair 432C and 433C to provide for electrical connection allowing data 532 to flow between RF module 130 and circuit 505 and to allow energy transmission from energy source 506 to RF module 130, in a way that is previously discussed for the example of FIG. 6B. In this example, VCC is modulated by data 532 so that only one pair of connectors, 432C and 433C, are needed. Housing 508 and housing 538 closed a ground loop for power transmission.

It is to be understood that the above description is intended to be illustrative, and not restrictive. For example, the implantable device can be any implantable medical device having an active electronic circuit. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. An implantable far-field telemetry module, including:
   an antenna;
   an radio-frequency (RF) module, coupled to the antenna, the RF module including an RF transmitter; and
   at least one data interface connector, coupled to the RF module, adapted to electrically connect the telemetry module to an implantable medical device for wired communication of data from the implantable medical device to the telemetry module for wireless communication of the data by the RF transmitter to an external device, the interface connector being at least one of a user-attachable connector and a detachable connector.

2. The telemetry module of claim 1, in which the implantable medical device is an implantable cardiac rhythm management device.

3. The telemetry module of claim 1, in which the antenna includes a conductor having approximately dimensions providing resonance at a frequency of an RF carrier signal of the telemetry module.

4. The telemetry module of claim 1, further including a lead carrying the antenna including at least one conductor.

5. The telemetry module of claim 1, in which the RF module further includes an energy source, coupled to the RF transmitter.

6. The telemetry module of claim 1, in which the RF transmitter includes:
an RF carrier generator including an RF oscillator and an output;
a modulator, coupled to the output of the RF carrier generator, to modulate the RF carrier with a first digital data stream, the modulator including an output representative of a modulated RF signal; and
an RF amplifier, coupled to the output of the modulator, to amplify the modulated RF signal.

7. The telemetry module of claim 6, in which the modulator includes an amplitude modulator including a switch driven by the first digital data stream to gate the output of the RF carrier generator.

8. The telemetry module of claim 6, in which the modulator includes a frequency modulator adopted to shift the frequency of the RF carrier with the first digital data stream.

9. The telemetry module of claim 6, in which the modulator includes a phase modulator adopted to shift the phase of the RF carrier with the first digital data stream.

10. The telemetry module of claim 1, in which the RF module further includes an RF receiver, coupled to the antenna.

11. The telemetry module of claim 10, in which the RF receiver includes an amplitude demodulator.

12. The telemetry module of claim 10, in which the RF receiver includes a frequency demodulator.

13. The telemetry module of claim 10, in which the RF receiver includes a phase demodulator.

14. The telemetry module of claim 1, further including a housing hermetically carrying the RF module.

15. The telemetry module of claim 1, in which the implantable medical device includes:
a device body, contained in a hermetically sealed housing, including at least a circuit and an energy source; and
a header, coupled to the body, including electrical conductor feedthroughs from the body, the feedthroughs terminating at connectors, the connectors including at least one connector adapted to mate to the interface connector of the telemetry module.

16. The telemetry module of claim 15, in which the at least one connector includes at least one socket allowing a plug-in connection between the RF module and the implantable medical device.

17. The telemetry module of claim 16, in which the RF module is within the interface connector.

18. The telemetry module of claim 17, further including mechanical fixation means for electrically and mechanically reinforcing the plug-in connection.

19. The telemetry module of claim 1, in which the interface connector is adapted to allow a user to re-attach the telemetry module to an implantable medical device after detachment.

20. An implantable far-field telemetry module, including:
an antenna;
an radio-frequency (RF) module, coupled to the antenna, the RF module including an RF transmitter; and
at least one interface connector, coupled to the RF module, adapted to attach the telemetry module to an implantable medical device, the interface connector being at least one of a user-attachable connector and a detachable connector, in which:
the antenna includes a first end and a second end;
the RF module is coupled to the first end of the antenna; and
the interface connector is coupled to the second end of the antenna and to the RF module through the antenna.

21. The telemetry module of claim 20, further including a lead carrying the antenna including at least one first conductor, coupled to the RF transmitter.

22. The telemetry module of claim 21, in which the first conductor being also adapted to communicate data between the RF module and the implantable medical device.

23. The telemetry module of claim 22, in which the first conductor is further adapted to supply power to the RF module from an energy source in the implantable medical device.

24. The telemetry module of claim 22, in which the RF module further includes a power supply input, coupled to the RF transmitter, and the lead includes at least one second conductor, coupled to the power supply input of the RF module, the second conductor adapted to supply power to the RF module from an energy source in the implantable medical device.

25. The telemetry module of claim 20, further including a first mechanical fixture, coupled to the RF module, to attach the RF module onto the implantable medical device, and in which the implantable medical device includes a second mechanical fixture adapted to join the first mechanical fixture.

26. The telemetry module of claim 25, in which the mechanical fixtures provide for a snap-on connection between the RF module and the implantable medical device.

27. The telemetry module of claim 20, in which the interface connector is adapted to provide a detachable connection between the telemetry module and the implantable medical device.

28. A method including:
connecting a user-attachable or detachable implantable far-field telemetry module to an implantable medical device to provide wired transmission of data from the implantable medical device to the telemetry module; and
using the telemetry module to provide far-field wireless telemetry of the data from the implantable medical device.

29. The method of claim 28, further including configuring the implantable medical device for providing cardiac rhythm management therapy.

30. The method of claim 28, in which a range of the far-field telemetry is at least six feet.

31. The method of claim 28, in which using the telemetry module to provide telemetry for the implantable medical device includes at least one of:
transmitting real-time physiological data acquired by the implantable medical device;
extracting physiological data stored in the implantable medical device;
extracting therapy history data stored in the implantable medical device; and
extracting data indicating an operational status of the implantable medical device.

32. The method of claim 28, in which using the telemetry module to provide telemetry for the implantable medical device includes at least one of:
    programming the implantable medical device to acquire physiological data;
    programming the implantable medical device to perform at least one self-diagnostic test for a device operational status; and
    programming the implantable medical device to deliver at least one therapy.

33. The method of claim 28, in which connecting the telemetry module to the implantable medical device including joining at least one pair of connectors.

34. The method of claim 33, further including attaching at least a portion of the telemetry module to the implantable medical device using a user-attachable snap-on connector.

35. The method of claim 28, in which connecting the telemetry module to the implantable medical device including plugging a portion of the telemetry module into the implantable medical device.

36. The method of claim 28, further including detaching the telemetry module from the implantable medical device after the telemetry module has been connected the implantable medical device.

37. A method including:
    connecting a user-attachable or detachable implantable far-field telemetry module to an implantable medical device, and
    providing far-field telemetry for the implantable medical device using the telemetry module, including:
        receiving, via wired communication using an electrical conductor, a first data stream from the implantable medical device;
        generating a first radio-frequency (RF) carrier suitable for far-field data transmission from within a body;
        modulating the first RF carrier to be representative of the first data stream; and
        wirelessly transmitting the modulated first RF carrier.

38. The method of claim 37, further including configuring the implantable device for providing cardiac rhythm management therapy.

39. The method of claim 37, in which a range of the far-field telemetry is at least six feet.

40. The method of claim 37, further including powering the telemetry module by a battery contained within the telemetry module.

41. The method of claim 37, in which modulating the first RF carrier by the first data stream includes modulating an amplitude of the first RE carrier by the first data stream, modulating the amplitude of the first RF carrier includes gating the first RF carrier.

42. The method of claim 37, in which the providing telemetry further includes:
    receiving a wireless RF carrier signal modulated by a second data stream in an external programmer;
    demodulating the signal to recover the second data steam; and
    communicating, via an electrical conductor, the second data stream to the implantable medical device.

43. The method of claim 42, in which the second RF carrier is amplitude modulated by the second data stream in the external programmer, and demodulating the signal includes using an envelope detector.

44. The method, of claim 37, in which connecting the telemetry module to the implantable medical device including joining at least one pair of connectors.

45. The method of claim 44, further including attaching at least a portion of the telemetry module to the implantable medical device using a user-attachable snap-on connector.

46. The method of claim 37, in which connecting the telemetry module to the implantable medical device including plugging the telemetry module in to the implantable medical device.

47. The method of claim 37, further including disconnecting the telemetry module from the implantable medical device after the telemetry module has been connected the implantable medical device.

* * * * *

UNITED STATES PATENT AND TRADEMARK OFFICE
CERTIFICATE OF CORRECTION

PATENT NO. : 7,096,068 B2
APPLICATION NO. : 10/052496
DATED : August 22, 2006
INVENTOR(S) : Mass et al.

It is certified that error appears in the above-identified patent and that said Letters Patent is hereby corrected as shown below:

On the face page, in field (56), under "U.S. Patent Documents", in column 2, line 6, after "6,675,049" delete "B1" and insert -- B2 --, therefor.

On the face page, in field (56), under "U.S. Patent Documents", in column 2, line 9, after "6,920,360" delete "B1" and insert -- B2 --, therefor.

In column 16, line 9, in Claim 41, delete "RE" and insert -- RF --, therefor.

In column 16, line 25, in Claim 44, after "method" delete ",".

Signed and Sealed this

Twenty-eighth Day of November, 2006

JON W. DUDAS
*Director of the United States Patent and Trademark Office*